United States Patent
Ruch

(10) Patent No.: US 6,642,686 B1
(45) Date of Patent: Nov. 4, 2003

(54) SWIVEL ARM WITH PASSIVE ACTUATORS

(75) Inventor: Christof Ruch, München (DE)

(73) Assignee: BrianLAB AG, Kirchheim/Heimstetten (DE)

(*) Notice: Subject to any disclaimer, the term of this patent is extended or adjusted under 35 U.S.C. 154(b) by 0 days.

(21) Appl. No.: 10/094,421

(22) Filed: Mar. 8, 2002

(30) Foreign Application Priority Data

Nov. 9, 2001 (EP) ............................................ 01126462

(51) Int. Cl.$^7$ .............................................. G05B 19/04
(52) U.S. Cl. .............................. 318/568.21; 318/568.1; 318/568.23; 318/568.14; 318/568.16; 901/1
(58) Field of Search ..................... 318/568.11, 568.1, 318/568.14, 568.16, 568.21, 568.23; 901/1

(56) References Cited

U.S. PATENT DOCUMENTS

| | | | | |
|---|---|---|---|---|
| 5,173,803 A | * | 12/1992 | Heller ........................ | 359/384 |
| 5,704,253 A | * | 1/1998 | Book et al. .............. | 74/490.01 |
| 5,820,623 A | * | 10/1998 | Ng ................................ | 606/1 |
| 5,828,197 A | | 10/1998 | Martin et al. ................ | 318/567 |
| 5,952,796 A | * | 9/1999 | Colgate et al. ................ | 318/1 |
| 6,199,812 B1 | * | 3/2001 | Schepbach .................. | 248/324 |
| 6,231,526 B1 | | 5/2001 | Taylor et al. ............... | 600/587 |

OTHER PUBLICATIONS

Davies, B.L. et al. "Robotic Surgery at Imperial College London." *Proceedings of the International Conference on Systems, Man and Cybernetics.* Oct. 17–20, 1993.

Radetzky, Arne. "ROBO–SIM: A Simulator for Minimally Invasive Neurosurgery using a Passive Manipulator," Online. Jan. 7, 2002. Available: www.ism–austria.at/arne/ara/robosim/robosim.html.

* cited by examiner

Primary Examiner—Bentsu Ro
Assistant Examiner—Rina I. Duda
(74) Attorney, Agent, or Firm—Renner, Otto, Boisselle & Sklar, LLP

(57) ABSTRACT

A swivel arm includes a fixing device for an instrument and at least one pivot, such that the swivel arm can be moved. At least one sensor on at least one pivot detects the position and/or movement of the at least one pivot. A controllable, passive actuator for the at least one pivot can brake and/or prevent a movement of the pivot. A control device guides the controllable, passive actuator on the basis of the position data and/or movement data transmitted from the at least one sensor and based on data of the target object. The passive actuator can be guided in such a way that an instrument connected to the swivel arm can perform only one or a number of predetermined movements.

12 Claims, 2 Drawing Sheets

SWIVEL ARM WITH PASSIVE ACTUATORS

TECHNICAL FIELD

The present invention relates to a swivel arm with passive actuators, in particular to be used in the field of computer-aided surgery for stereotactic applications.

DESCRIPTION OF RELATED ART

A pivoting arm is known from U.S. Pat. No. 5,820,623 which serves to support and position medical instruments. In this respect, a drive device is provided comprising a servomotor, to move a pivoting element of the arm.

A device and a method are known from U.S. Pat. No. 5,952,796 for guiding the movements of an operator, e.g. to assist a person in moving a load by using a control motor.

U.S. Pat. No. 5,704,253 discloses a device for guiding a movement along a given trajectory.

SUMMARY OF THE INVENTION

It is an object of the present invention to propose a swivel arm, a system comprising a swivel arm and a method for guiding a swivel arm, which can be used to assist in examining or treating a body.

This object is solved by the devices and methods defined in the independent claims. Advantageous embodiments follow from the sub-claims.

One end of the swivel arm in accordance with the invention can be fixed to a suitable support such as for example a table or a medical device and comprises at least one pivot and preferably a number of pivots, such that the fixed swivel arm can be moved with at least one degree of freedom, preferably with two, three, four, five or more degrees of freedom. In this respect, a pivot can enable a rotational movement or a tilting movement, such that for example a ball bearing can be used to enable a rotational movement or a hinge to enable a tilting movement. A telescopic element, for example, is also to be understood as a pivot in the sense of the invention, by means of which a movement in the axial direction of the telescopic element is possible. In general, the swivel arm is to be designed by attaching at least one pivot in such a way that a movement can be performed with at least one degree of freedom. On the at least one pivot, a sensor is provided with which the position or movement of the at least one pivot can be determined. A controllable passive actuator, for example a controllable brake, is furthermore provided on the at least one pivot in accordance with the invention, to release the movement of the swivel arm at the specific pivot, to impede and/or brake said movement, or even to render it entirely impossible, with a variable resistance force, i.e. to arrest the pivot in a particular position. In accordance with the invention, the controllable passive actuator is guided by a control device which can determine the current position of the swivel arm as a whole, in particular the position of an instrument or the tip of an instrument connected to the swivel arm, based on the sensor data of the at least one pivot sensor. In accordance with the invention, data on a target object to be examined or treated with the instrument, for example a body or part of a body, are detected, for example by CT or MRI, before or while the arm is used, and used by the control device to output control signals, determined in combination with the position of the instrument determined from the sensor signals, to the passive actuators to thus impede and/or decelerate or facilitate and/or simplify a particular movement of the swivel arm at the respective pivots.

The swivel arm in accordance with the present invention thus enables an operator to relatively simply and exactly move an instrument guided by the swivel arm with the aid of the control device to a desired position or along a given path, or also to move it within a desired range e.g. to perform a method planned before using the instrument connected to the swivel arm.

Since only passive actuators, for example controllable brake elements, are used in the individual pivots in accordance with the invention, no active element such as for example a motor is required, such that the swivel arm can be manufactured cost-effectively, comprises a simple mechanism, can be guided simply and is relatively light. Consequently, no driving element is required for the swivel arm, since the force required to move the swivel arm is applied by an operator and said movement is directed to the desired position by the swivel arm in accordance with the invention in co-operation with the control device, by employing the passive actuators in a targeted and dosed way.

Thus, an operator can for example be given a haptic feedback or a tactile feedback as to whether for example the direction of movement in which the swivel arm is moved by the operator is correct or not. To this end, a braking force applied to the pivot by the actuator can for example be increased when the operator moves the swivel arm in a direction which does not correspond to a desired or planned direction, and the braking force can be reduced when the movement of the swivel arm by the operator is in the desired direction. The passive actuator provided on one or on each pivot in accordance with the invention can even block the respective pivot completely, if moving the swivel arm further would cause the instrument connected to the swivel arm to penetrate a sensitive area, thus for example avoiding undesired injuries or incisions.

The feedback can advantageously be designed in such a way that the force opposing a movement of the swivel arm initiated by the operator is dosed in such a way that the operator can "sense" particular areas in which for example an instrument connected to the arm is situated. Thus, based on imaging performed beforehand on a body to be treated, particular values of a resistance force can for example be assigned to particular areas or structures, such as for example veins, tendons, bones, soft tissue etc., by a processing step carried out before treatment, for example suitably segmenting the body, said resistance force being opposed for example by a movement of an instrument connected to the arm, if for example the tip of the instrument approaches or enters such an area. In this respect, different resistance values can be assigned to different structures and/or their near vicinity, such that the passive actuators of the arm oppose movements towards or through the corresponding areas, using exactly dosed braking or supporting forces. Using such a tactile feedback, an operator can "sense" in which area an instrument connected to the arm is situated, by assigning different values of movement resistance to different areas or structures.

The swivel arm and in particular each actuator is preferably designed in such a way that the force of e.g. 2 kN which may be applied by a person can be supported, i.e. an operator cannot move a pivot fixed by the actuator, not even via leverage acting on partial elements of the swivel arm.

The instrument connected to the swivel arm is preferably a medical and/or surgical instrument and is attached to a partial element of the swivel arm either directly or via an adaptor or suitable support which can be moved when the arm is attached to a supporting device. Thus, for example, a nail, a screw, an endoscope, a microscope, a biopsy needle, a cutting device such as for example a scalpel, a catheter or a catheter guide, a drill, a drilling template, a cutting block or a cutting template or the like can be used as an instrument, which can be connected to the swivel arm and moved to a desired position, along a given trajectory or in a particular area by the control device.

The invention further relates to a system comprising a swivel arm such as described above and an input device for inputting e.g. control data for the control device such as for example the type and/or dimensions of the instrument used, the type of desired method to be performed and/or data on the target object, for example the body and/or part of the body to be treated or examined, said data being obtained for example by computer topography (CT), nuclear spin resonance imaging (MRI), ultrasonic examination, positron emission topography (PET) or other suitable methods. Thus, prior to neurosurgery, the operator can, on the basis of for example three-dimensional data of a part of the body to be treated, e.g. a brain, define an area in which a cutting instrument and/or its cutting tip connected to the swivel arm can move, using a suitable planning software, thus ensuring that no incision can be made in tissue outside said area and that only tissue in the area of the tumour and a given area around the tumour can be removed using the cutting instrument. To this end, the body or part of the body to be treated must be registered, i.e. the relative position of the swivel arm and/or the instrument connected to it and the body to be treated has to be detected. This can be done, for example, using passive markers. Such methods are known in the prior art and will not be described in more detail here.

The tactile feedback described above can also be realized through corresponding control data for the control device, i.e. for example by assigning particular resistance forces or braking forces to be realized by the actuators to particular body structures.

Preferably, a display or data output device can be provided in the system in accordance with the invention, for example in the form of a monitor on which for example position-related data on the instrument connected to the swivel arm and/or on the body or part of the body to be treated are displayed, thus showing an operator in which area of the body the instrument is currently.situated or what the near or wider vicinity of the treatment area looks like.

In accordance with a further aspect of the invention, a method is proposed for guiding the swivel arm described above comprising at least one pivot, using a guidable passive actuator, such that an instrument connected to the swivel arm can only perform one or more given movements, due to the control signals influencing at least one passive actuator, under the influence of an external force from an operator, for example said instrument can be guided to a particular position, by the at least one passive actuator braking movements diverging from this position and releasing movements converging on this position, wherein a particular path to said position which the instrument is to pass through can also be given. Furthermore, it is possible to define for example a radius of action for the medical instrument, in which it can be moved, wherein at least one controllable passive actuator can increasingly impede or brake movement of the instrument towards an area which is inaccessible for the instrument and for example creates a complete blockage at the border of the area.

The guiding method in accordance with the invention can advantageously be designed such that a movement deviating from a desired movement is braked more strongly, the more the actual movement deviates from the desired movement, so giving the operator a haptic feedback.

The control properties and/or control algorithms of the guiding method in accordance with the invention can advantageously be determined prior to employing the swivel arm, for example using a suitable planning software. In this respect, for example using three-dimensional data of the target object, a location or area in a body or part of a body to be treated or examined can be given, to which the instrument connected to the swivel arm is to be positioned or moved, wherein the path which the instrument is to pass along to reach the desired position can also be given. This can be the case for example in ENT surgery, when an instrument is to be guided for example through a nostril to reach a given position. For surgery in the area of the hip or the knee, as well as in spinal surgery, particular elements such as for example screws, nails, drills, cutting tools, drilling templates or cutting blocks can also be guided to desired points of the part of the body to be treated, in order for example to apply a screw to a desired position, such that it can easily be screwed into the correct position by an operator. Furthermore, it is also possible to define so-called "no-go-zones" in which the instrument connected to the swivel arm Is not allowed to interfere, for example In the case of surgery which is only to be performed in a particular area and in which it should be ensured that adjacent areas are not affected by the surgery, such as for example neurosurgery.

BRIEF DESCRIPTION OF DRAWINGS

An embodiment of the method in accordance with the invention will be illustrated in principle on the basis of an example embodiment. There is shown.

DETAILED DESCRIPTION OF THE INVENTION

Figure 1:
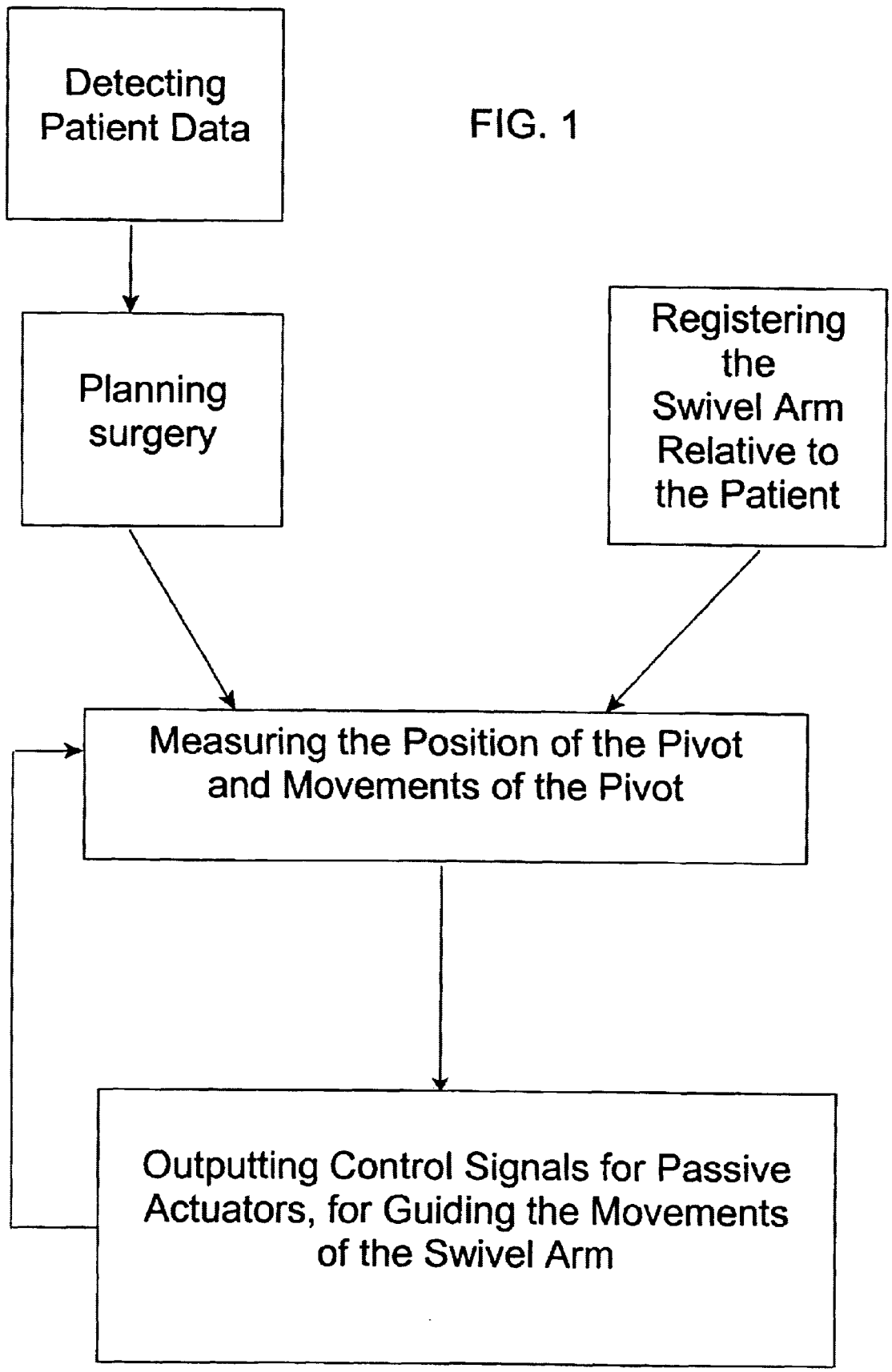
FIG. 1 a flow chart for preparing and performing the guiding of a swivel arm.

As shown in FIG. 1, patient data are detected in a first step by means of suitable methods, such as for example CT, MR, PET or other methods, thereby obtaining for example three-dimensional data of an object or part of a body to be examined or treated. Based on said detected patient data, an incision which is actually to be performed is planned, preferably using a suitable planning software, wherein for example particular trajectories to be passed through or positions to be approached or even areas on the body to be treated can be predetermined, in which surgery must not take place.

The swivel arm is registered relative to the patient, i.e. the patient and the swivel arm are brought into a mutually defined position relationship or, for example, the exact position of a patient is determined on the basis of markers connected to the patient, wherein the swivel arm is or is to be attached to a point which fixed relatively.

Based on the desired or undesired movements and/or movement directions of the swivel arm predetermined by the surgical planning, and using the patient data, the positions or movements of the individual pivots of the swivel arm are then continuously measured, control signals being outputted to the passive actuators provided on the pivots, according to the desired operation to be carried out, to guide the movements of me swivel arm by an operator, i.e. movements by individual pivots in undesired directions can for example be braked or blocked, and movements in one or a number of desired or permitted directions ran be released by the passive actuators.

Figure 2:
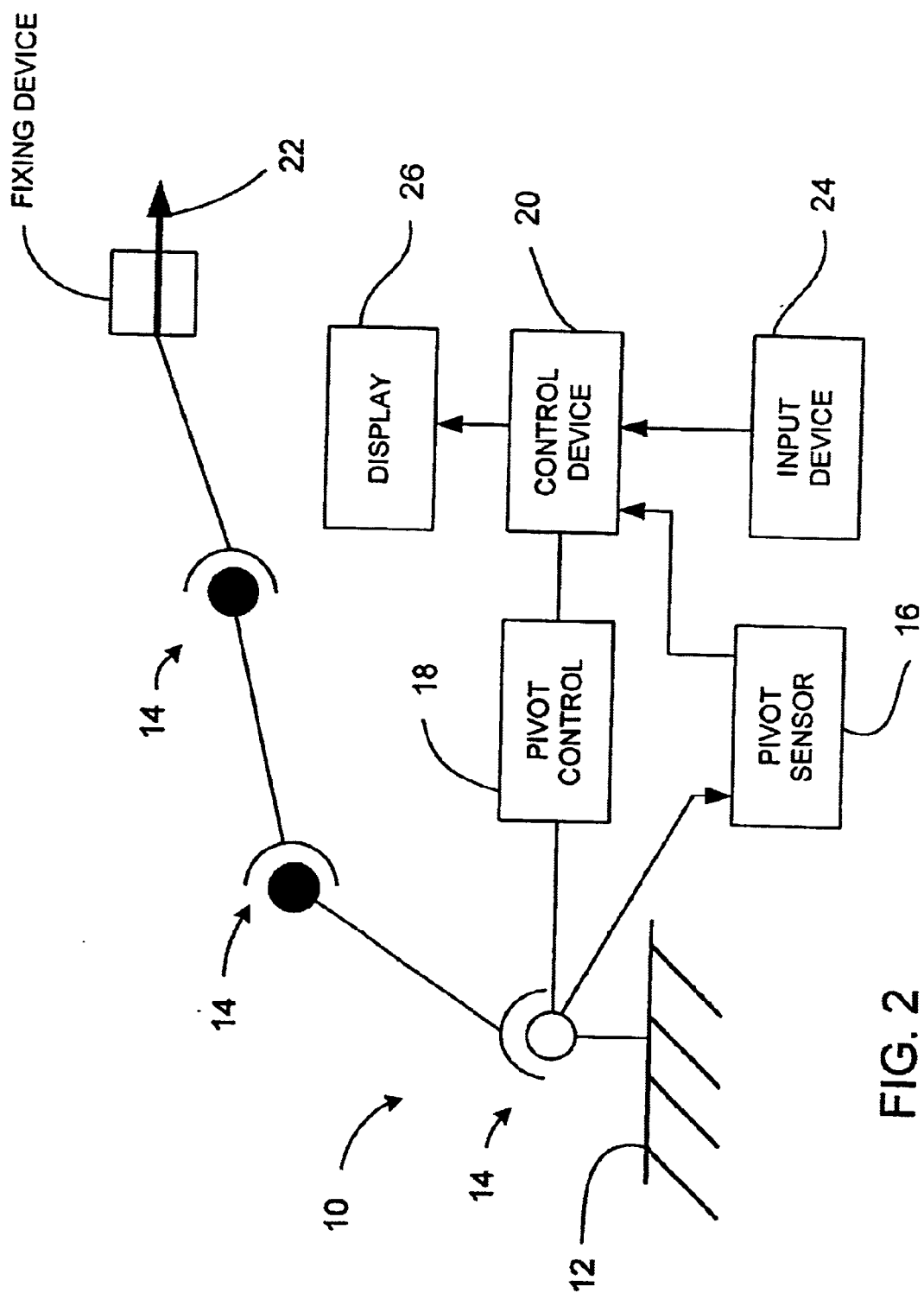
FIG. 2 is a diagrammatic illustration of a swivel arm apparatus and system in accordance with the present invention.

With reference to FIG. 2, one end of the swivel arm 10 in accordance with the invention can be fixed to a suitable support 12 such as for example a table or a medical device and comprises at least one pivot 14 and preferably a number of pivots 14, such that the fixed swivel arm 10 can be moved with at least one degree of freedom, preferably with two, three, four, five or more degrees of freedom. In this respect, a pivot 14 can enable a rotational movement or a tilting movement, such that for example a ball bearing can be used to enable a rotational movement or a hinge to enable a tilting movement. A telescopic element, for example, is also to be understood as a pivot in the sense of the invention, by means of which a movement in the axial direction of the telescopic element is possible. In general, the swivel arm 10 is to be designed by attaching at least one pivot 14 in such a way that a movement can be performed with at least one degree of freedom. On the at least one pivot 14, a sensor 16 is provided with which the position or movement of the at least one pivot 14 can be determined. A controllable passive actuator 18, for example a controllable brake, is furthermore provided on the at least one pivot 14 in accordance with the invention, to release the movement of the swivel arm 10 at the specific pivot 14, to impede and/or brake said movement, or even to render it entirely impossible, with a variable resistance force, i.e. to arrest the pivot in a particular position. In accordance with the invention, the controllable passive actuator 18 is guided by a control device 20 which can determine the current position of the swivel arm as a whole, in particular the position of an instrument 22 or the tip of an instrument connected to the swivel arm 10, based on the sensor data of the at least one pivot sensor 16. In accordance with the invention, data on a target object to be examined or treated using the instrument, for example a body or part of a body, are detected, for example by CT or MRI, before or while the arm 10 is used, and used by the control device 20 to output control signals, determined in combination with the position of the instrument 22 determined from the sensor signals, to the passive actuators 18 to thus impede and/or decelerate or facilitate and/or simplify a particular movement of the swivel arm 10 at the respective pivots 14.

The swivel arm in accordance with the present invention thus enables an operator to relatively simply and exactly move an instrument 22 guided by the swivel arm 10 with the aid of the control device 20 to a desired position or along a given path, or also to move it within a desired range e.g. to perform a method planned before using the instrument connected to the swivel arm 10.

Since only passive actuators 18, for example controllable brake elements, are used in the individual pivots 14 in accordance with the invention, no active element such as for example a motor is required, such that the swivel arm 10 can be manufactured cost effectively, comprises a simple mechanism, can be guided simply and is relatively light. Consequently, no driving element is required for the swivel arm 10, since the force required to move the swivel arm is applied by an operator and said movement is directed to the desired position by the swivel arm 10 in accordance with the invention in co-operation with the control device 20, by employing the passive actuators 18 in a targeted and dosed way. Thus, an operator can for example be given a haptic feedback or a tactile feedback as to whether for example the direction of movement in which the swivel arm 10 is moved by the operator is correct or not. To this end, a braking force applied to the pivot 14 by the actuator 18 can for example be increased when the operator moves the swivel arm 10 in a direction which does not correspond to a desired or planned direction, and the braking force can be reduced when the movement of the swivel arm 10 by the operator is in the desired direction. The passive actuator 18 provided on one or on each pivot 14 in accordance with the invention can even block the respective pivot 14 completely, if moving the swivel arm 10 further would cause the instrument 22 connected to the swivel arm to penetrate a sensitive area, thus for example avoiding undesired injuries or incisions.

The feedback can advantageously be designed in such a way that the force opposing a movement of the swivel arm 10 initiated by the operator is dosed in such a way that the operator can "sense" particular areas in which for example an instrument connected to the arm is situated. Thus, based on imaging performed beforehand on a body to be treated, particular values of a resistance force can for example be assigned to particular areas or structures, such as for example veins, tendons, bones, soft tissue etc., by a processing step carried out before treatment, for example suitably segmenting the body, said resistance force being opposed for example by a movement of an instrument connected to the arm, if for example the tip of the instrument approaches or enters such an area. In this respect, different resistance values can be assigned to different structures and/or their near vicinity, such that the passive actuators of the arm oppose movements towards or through the corresponding areas, using exactly dosed braking or supporting forces. Using such a tactile feedback, an operator can "sense" in which area an instrument connected to the arm is situated, by assigning different values of movement resistance to different areas or structures.

The swivel arm 10 and in particular each actuator 18 is preferably designed in such a way that the force of e.g. 2 kN which may be applied by a person can be supported, i.e. an operator cannot move a pivot 14 fixed by the actuator 18, not even via leverage acting on partial elements of the swivel arm.

The instrument 22 connected to the swivel arm is preferably a medical and/or surgical instrument and is attached to a partial element of the swivel arm 10 either directly or via an adaptor or suitable support which can be moved when the arm is attached to a supporting device. Thus, for example, a nail, a screw, an endoscope, a microscope, a biopsy needle, a cutting device such as for example a scalpel, a catheter or a catheter guide, a drill, a drilling template, a cutting block or a cutting template or the like can be used as an instrument, which can be connected to the swivel arm 10 and moved to a desired position, along a given trajectory or in a particular area by the control device 20.

The invention further relates to a system comprising a swivel arm 10 such as described above and an input device 24 for inputting e.g. control data for the control device such as for example the type and/or dimensions of the instrument used, the type of desired method to be performed and/or data on the target object, for example the body and/or part of the body to be treated or examined, said data being obtained for example by computer topography (CT), nuclear spin resonance imaging (MRI), ultrasonic examination, positron emission topography (PET) or other suitable methods. Thus, prior to neurosurgery, the operator can, on the basis of for example three-dimensional data of a part of the body to be treated, e.g. a brain, define an area in which a cutting instrument and/or its cutting tip connected to the swivel arm can move, using a suitable planning software, thus ensuring that no incision can be made in tissue outside said area and that only tissue in the area of the tumour and a given area around the tumour can be removed using the cutting instrument. To this end, the body or part of the body to be treated must be registered, i.e. the relative position of the swivel arm and/or the instrument connected to it and the body to be treated has to be detected. This can be done, for example, using passive markers. Such methods are known in the prior art and will not be described in more detail here.

The tactile feedback described above can also be realized through corresponding control data for the control device 20, i.e. for example by assigning particular resistance forces or braking forces to be realized by the actuators 18 to particular body structures.

Preferably, a display 26 or data output device can be provided in the system in accordance with the invention, for example in the form of a monitor on which for example position-related data on the instrument connected to the swivel arm and/or on the body or part of the body to be treated are displayed, thus showing an operator in which area of the body the instrument is currently situated or what the near or wider vicinity of the treatment area looks like.

What is claimed is:

1. A swivel arm for assisting in examining or treating a body, said swivel arm comprising:

a fixing device for an instrument, to examine or treat a target object;

at least one pivot to move the fixing device for the instrument;

at least one sensor on the at least one pivot, to detect the position and/or movement of the at least one pivot;

a controllable, passive actuator for the at least one pivot, said actuator applying a braking force to the at least one pivot in response to a control signal, said braking force restricting or preventing a movement of the pivot; and a control device for providing a control signal to the controllable passive actuator on the basis of the position data and/or movement data transmitted from the at least one sensor and based on data of the target object, wherein the control signal provided to the actuator causes (i) an increasing braking force as an operator moves the swivel arm in a direction that does not correspond to a predetermined desired direction and (ii) a decreasing braking force as the operator moves the swivel arm in a predetermined desired direction.

2. A swivel arm according to claim 1, wherein the instrument is at least one of a nail, a screw, an endoscope, a microscope, a cutting device, a scalpel, a biopsy needle, a catheter, a catheter guide, a drill, a drilling template or a cutting template.

3. A swivel arm according to claim 1, wherein the at least one pivot enables a rotational movement and/or a tilting movement.

4. A swivel arm according to claim 1, wherein at least two, pivots are provided on the swivel arm.

5. A swivel arm according to claim 1, wherein the at least one controllable, passive actuator on the pivot is designed in such a way that it can hold the force applied to the pivot by a human being.

6. A system comprising a swivel arm according to claim 1 and an input device for inputting data of a target object to be examined or treated by the instrument and/or for inputting control data for a method to be performed.

7. A system according to claim 6, comprising a display, for displaying position data and/or the vicinity of the instrument guided by the swivel arm.

8. A method for guiding a swivel arm or a system according to claim 6, wherein the at least one controllable, passive actuator is guided in such a way that an instrument connected to the swivel arm can perform only one or a number of predetermined movements.

9. A method according to claim 8, wherein the movements or movement areas to be released by the control method are predetermined prior to guiding the passive actuators of the swivel arm.

10. A method according to claim 8, wherein three-dimensional data of the target object to be examined or treated by the instrument is used for guiding and/or for guidance planning, and for realizing a tactile feedback.

11. A method according to claim 8, wherein the swivel arm is guided in such a way that an operator is given a haptic feedback.

12. A swivel arm according to claim 1, wherein the control signal causes braking forces based on pre-set resistance force values independent of a body structure's natural resilience.

* * * * *